United States Patent
Rao et al.

(10) Patent No.: US 7,651,705 B2
(45) Date of Patent: Jan. 26, 2010

(54) HERBAL COMPOSITION FOR THE TREATMENT OF GASTRIC ULCER

(75) Inventors: Janaswamy Madhusudana Rao, Hyderabad Andhra Pradesh (IN); Upparapalli Sampathkumar, Hyderabad Andhra Pradesh (IN); Boggavarapu Subrahmanya Sastry, Hyderabad Andhra Pradesh (IN); Jhillu Singh Yadav, Hyderabad Andhra Pradesh (IN); Kondapuram Vijaya Raghavan, Hyderabad Andhra Pradesh (JP); Gautam Palit, Lucknow (IN); Dwaraka Nath Bhalla, Lucknow (IN); Deepak Rai, Lucknow (IN); Panniyampally Madhavankutty Varier, Kerala (IN); Trikovil Sankaran Muraleedharan, Kerala (IN); Kollath Muraleedharan, Kerala (IN)

(73) Assignee: Council of Scientific & Industrial Research, New Delhi (IN)

( * ) Notice: Subject to any disclaimer, the term of this patent is extended or adjusted under 35 U.S.C. 154(b) by 25 days.

(21) Appl. No.: 10/695,471

(22) Filed: Oct. 28, 2003

(65) Prior Publication Data

US 2005/0089583 A1    Apr. 28, 2005

(51) Int. Cl.
*A01N 65/00*      (2006.01)
*A61K 36/8965*  (2006.01)
*A61K 36/484*    (2006.01)

(52) U.S. Cl. .................... 424/725; 424/757; 514/924
(58) Field of Classification Search ............... 424/744, 424/757, 725; 514/925, 783
See application file for complete search history.

(56) References Cited

U.S. PATENT DOCUMENTS

| | | | |
|---|---|---|---|
| 2,704,258 A | * | 3/1955 | Haney |
| 4,022,921 A | * | 5/1977 | Sakakibara et al. |
| 4,544,551 A | * | 10/1985 | Hong-Yue |
| 4,851,224 A | * | 7/1989 | McAnalley |
| 4,913,909 A | * | 4/1990 | Hara et al. |
| 7,025,995 B2 | * | 4/2006 | Palpu et al. |

FOREIGN PATENT DOCUMENTS

| | | | |
|---|---|---|---|
| CN | 1129570 A | * | 8/1996 |
| JP | 54067038 A | * | 5/1979 |

OTHER PUBLICATIONS

Goel, R. K. et al. Indian Journal of Pharmacology (Jul. 2002), 34(2): 100-110. Anti-ulcer drugs from indigenous sources with emphasis on *Musa sapientum, Tamrabhasma, Asparagus racemosus* and *Zingiber officinale*.*

Dehpour, A. R. et al. International Journal of Pharmaceutics (1995), 119(2): 133-138. Antiulcer activities of liquorice and its derivatives in experimental gastric lesion induced by ibuprofen in rats.*
Johnson, T. CRC Ethnobotany Desk Reference (1999), CRC Press LLC, Boca Raton, Florida, p. 842, [26191].*
Goel, R. L. et al. Journal of Ethanopharmacology (1986), 18(1): 33-44. Anti-ulcerogenic effect of bananan powder *Musa-sapeientum*-var-*paradisiaca* and its effect on mucosal resistance.*
Khrenova, D. et al. Farmatsiya (1986), 35(3): 46-48. Qualitative phytochemical analysis of an antiulcerous drugs prepared from plants.*
http://www.henriettesherbal.com/eclectic/usdisp/ferula-asaf.html. Remington, et al. The Dispensatory of the United States of America. Downloaded Jan. 21, 2007.*
U1, Khrenova, D. et al. Farmatsiya (1986), 35(3): 46-48. Qualitative phytochemical analysis of an antiulcerous drugs prepared from plants.*
Christina, A.J.M. et al. Methods Find Exp Clin Pharmacol (Mar. 2002), 24(2): 77-79. Modulatory effet of *Cyclea peltata* Lam. on stone formation induced by ethylene glycol treatment in rats.*
Lewis, D. A. et al. J of Ethnopharmacology (1999), 65: 283-288. A natural flavonoid present in unripe plantain banana pulp (*Musa sapientum* L. var. *paradisiaca*) protects the gastric mucosa from aspirin-induced erosions.*
Rao, I. G. et al., Chemophere (Sep. 2001), 44(8): 1691-1695. Combinations of *Azadirachta indica* and *Cedrus deodara* oil with piperonyl butoxide, MGK-264 and *Embelia ribes* against *Lymnaea acuminata*.*
Singh, A. et al. Indian Journal of Experimental Biology (2001), 39(3): 263-268. Molluscicidal activity of Lawsonia inermis and its binary and tertiary combinations with other plant derived molluscicides. Abstract.*
Rao, V. L. N., et al. Indian Pharmacist (1948), 4: 14-17 and 32. Pharmacognosy of *Carum roxburghianum* Benth.*
Hankey, W. F. Am. Drug (1907), 49: 360-362. The assay processes of the U. S. Pharmacopoeia, VIII. Abstract.*
Purohit, M. G. et al. Indian Journal of Pharmaceutical Science (1996), 58(3): 110-112. Antiulcer and anticatatonic activity of alcoholic extract of Evolvulus alsinoides.).*
P.K. Warrier, Indian Medicinal Plants—A compendium of 500 species (1994-1996) vol. 1, p. 218-219, published by orient Longman, Chennai.

(Continued)

*Primary Examiner*—Michele Flood
(74) *Attorney, Agent, or Firm*—John P. White; Cooper & Dunham LLP

(57) ABSTRACT

Provided herein are synergistic herbal compositions for the treatment of gastric ulcer, said composition essentially comprising powdered plant parts of *Asparagus racemosus, Glycyrrhiza glabra, Sesamum indicum, Musa sapientum* and *Trachyspermum roxburghianum* and optionally, powdered plant parts of *Cyclea peltata, Embelia ribes, Coriandrum sativum Ferulaasafetida, Aloe barbadensis* and *Evolvulus aisinodes* along with one or more pharmaceutically acceptable additives/carriers, processes for preparing such compositions and methods for treating gastric ulcers using such compositions.

8 Claims, No Drawings

OTHER PUBLICATIONS

P.K. Warrier, Indian Medicinal Plants—A compendium of 500 species (1994-1996) vol. 3, p. 86-87, published by orient Longman, Chennai.

P.K. Warrier, Indian Medicinal Plants—A compendium of 500 species (1994-1996) vol. 3, pp. 11-12, published by orient Longman, Chennai.

P.K. Warrier, Indian Medicinal Plants—A compendium of 500 species (1994-1996) vol. 4, p. 78, published by orient Longman, Chennai.

P.K. Warrier, Indian Medicinal Plants—A compendium of 500 species (1994-1996) vol. 3, p. 297-299, published by orient Longman, Chennai.

P.K. Warrier, Indian Medicinal Plants—A compendium of 500 species (1994-1996) vol. 2, p. 368-369, published by orient Longman, Chennai.

P.K. Warrier in Indian Medicinal Plants—A compendium of 500 species (1994-1996) vol. 2, p. 184-185, published by orient Longman, Chennai.

P.K. Warrier, Indian Medicinal Plants—A compendium of 500 species (1994-1996) vol. 2, p. 277-278, published by orient Longman, Chennai.

P.K. Warrier , Indian Medicinal Plants—A compendium of 500 species (1994-1996) vol. 3, p. 13-16, published by orient Longman, Chennai.

K.M. Nadkarni, Indian Materia Medica (1976) vol. 1, pp. 74-76, published by Popular Prakashan Pvt. Ltd., Mumbai.

K.M. Nadkarni, Indian Materia Medica (1976) vol. 1, p. 582, published by Popular Prakashan Pvt. Ltd., Mumbai.

K.M. Nadkarni, Indian Materia Medica (1976) vol. 1, pp. 1027-1028, published by Popular Prakashan Pvt. Ltd, Mumbai.

K.M. Nadkarni, Indian Materia Medica (1976) vol. 1, p. 531, published by Popular Prakashan Pvt. Ltd., Mumbai.

K.M. Nadkarni, Indian Materia Medica (1976) vol. 1, pp. 822-825, published by Popular Prakashan Pvt. Ltd., Mumbai.

K.M. Nadkarni, Indian Materia Medica (1976) vol. 1, pp. 1028-1030, published by Popular Prakashan Pvt. Ltd., Mumbai.

K.M. Nadkarni, Indian Materia Medica (1976) vol. 1, p. 478, published by Popular Prakashan Pvt. Ltd., Mumbai.

K.M. Nadkarni, Indian Mateira Medica (1976) vol. 1, pp. 381-382, published by Popular Prakashan Pvt. Ltd., Mumbai.

K.M. Nadkarni in Indian Materia Medica (1976) vol. 1, p. 537, published by Popular Prakashan Pvt. Ltd., Mumbai.

* cited by examiner

HERBAL COMPOSITION FOR THE TREATMENT OF GASTRIC ULCER

FIELD OF THE INVENTION

The present invention relates to a synergistic herbal composition for the treatment of gastric ulcer. The present invention also relates to a method for the preparation of the composition. The present invention further relates to a process for the treatment of gastric ulcer using the composition.

BACKGROUND AND PRIOR ART TO THE INVENTION

Various theories have been proposed with respect to a cause of ulcer in human. In particular, it has been elucidated that stress, taking of non-steroidal anti-inflammatory drugs for curing rheumatic diseases, and the like are closely related to ulcer formation, mainly due to relatively excess gastric or duodenal acid secretion. Accordingly it is important to suppress the acid secretion in order to prevent ulcer formation and to cure it.

On the other hand it has been considered that *Helicobacter pylori*, which is a rod normally existing in stomach, generates ammonia due to its strong urease activity, thereby inducing ulcer. Since, it persistently lives within mucus and mucosa, it becomes the greatest cause for recurrence of ulcer. Accordingly, it has been considered that the recurrence of ulcer can be prevented, if this bacterium is sterilized.

References may be made to K. M. Nadkarni in Indian Materia Medica (1976) Vol. 1, p 74-76, 155, published by Popular Prakashan Pvt. Ltd., Mumbai; K. R. Kirtikar in Indian Medicinal Plants (1975) Vol. 4, p 2505 published by Bishen Singh Mahendrapal Singh, Dehradun and P. K. Warrier in Indian Medicinal Plants- A compendium of 500 species (1994-1996) Vol. 1, p 103 for the various medicinal properties of *Aloe barbadensis*.

References may be made to K. M. Nadkarni in Indian Materia Medica (1976) Vol. 1, p 155 published by Popular Prakashan Pvt. Ltd., Mumbai; K. R. Kirtikar in Indian Medicinal Plants (1975) Vol. 4, p 2249 published by Bishen Singh Mahendrapal Singh, Dehradun; P. K. Warrier in Indian Medicinal Plants- A compendium of 500 species (1994-1996) Vol. 1, p 218, and K. Narayana Iyer and M. Kolammal in Pharmacognosy of Ayurvedic Drugs (1963) Series 1, No. 6, p. 48 published by Department of Pharmacognosy, University of Kerala, Trivandrum for the various medicinal properties of *Asparagus racemosus*.

References may be made to K. M. Nadkarni in Indian Materia Medica (1976) Vol. 1, p 582 published by Popular Prakashan Pvt. Ltd., Mumbai; K. R. Kirtikar in Indian Medicinal Plants (1975) Vol. 1, p. 728 published by Bishen Singh Mahendrapal Singh, Dehradun; P. K. Warrier in Indian Medicinal Plants- A compendium of 500 species (1994-1996) Vol. 3, p 84, 86-87; The Wealth of India (1950-1980) Vol. 4, p. 152-153, published by Council of Scientific and Industrial Research; S. S. Handa in Indian Herbal Pharmacopeia (1998), p. 96, published by Regional Research Laboratory, Jammu and IDMA, Mumbai; Y. K. Sarin in Illustrated lanual of herbal drugs used in Ayurveda (1996), p. 116, and The Ayurvedic Pharmacopoeia of India, Vol. 1, p. 128, published by Ministry of Health and Family Welfare, India for the various medicinal properties of *Glycyrrhiza glabra*.

References may be made to K. M. Nadkarni in Indian Materia Medica (1976) Vol. 1, p. 1127-28, published by Popular Prakashan Pvt. Ltd., Mumbai; K. R. Kirtikar in Indian Medicinal Plants (1975) Vol. 3, p 1858-89 published by Bishen Singh Mahendrapal Singh, Dehradun; P. K. Warrier in Indian Medicinal Plants- A compendium of 500 species (1994-1996) Vol. 5, p 104, and The Wealth of India (1950-1980) Vol. 9, p. 290, published by Council of Scientific and Industrial Research for the various medicinal properties of *Sesamum indicum*.

References may be made to K. M. Nadkarni in Indian Materia Medica (1976) Vol. 1, p 531, published by Popular Prakashan Pvt. Ltd., Mumbai; P. K. Warrier in Indian Medicinal Plants- A compendium of 500 species (1994-1996) Vol. 3, p. 11-12, and K. Narayana Iyer and M. Kolammal in Pharmacognosy of Ayurvedic Drugs (1963) Series 1, No. 6, p. 1, published by Department of Pharmacognosy, University of Kerala, Trivandrum for the various medicinal properties of *Evolvulus alsinoides*.

References may be made to K. M. Nadkarni in Indian Materia Medica (1976) Vol. 1, p822-825, published by Popular Prakashan Pvt. Ltd., Mumbai; K. R. Kirtikar in Indian Medicinal Plants (1975) Vol. 4, p. 2454, published by Bishen Singh Mahendrapal Singh, Dehradun, and P. K. Warrier in Indian Medicinal Plants- A compendium of 500 species (1994-1996) Vol. 4, p 78 for the various medicinal properties of *Musa sapientum*.

References may be made to K. M. Nadkarni in Indian Materia Medica (1976) Vol. 1, p 1028-1030, published by Popular Prakashan Pvt. Ltd., Mumbai; P. K. Warrier in Indian Medicinal Plants- A compendium of 500 species (1994-1996) Vol. 3, p. 299, published by orient Longman, Chennai; The Wealth of India (1950-1980) Vol. 10, p. 271, published by Council of Scientific and Industrial Research; Y. K. Sarin in Illustrated lanual of herbal drugs used in Ayurveda (1996), p. 202, and The Ayurvedic Pharmacopoeia of India, Vol. 1, p. 3, published by Ministry of Health and Family Welfare, India for the various medicinal properties of *Trachyspermum roxburghianum*.

References may be made to K. M. Nadkarni in Indian Materia Medica (1976) Vol. 1, p. 478, published by Popular Prakashan Pvt. Ltd., Mumbai; K. R. Kirtikar in Indian Medicinal Plants (1975) Vol. 2, p. 1479, published by Bishen Singh Mahendrapal Singh, Dehradun; P. K. Warrier in Indian Medicinal Plants- A compendium of 500 species (1994-1996) Vol. 2, p. 368, published by orient Longman, Chennai; The Wealth of India (1950-1980) Vol. 3, p. 167, published by Council of Scientific and Industrial Research; Y. K. Sarin in Illustrated lanual of herbal drugs used in Ayurveda (1996), p. 290, and The Ayurvedic Pharmacopoeia of India, Vol. 1, p. 124, published by Ministry of Health and Family Welfare, India for the various medicinal properties of *Embelia ribes*.

References may be made to K. M. Nadkarni in Indian Materia Medica (1976) Vol. 1, p. 381-82, published by Popular Prakashan Pvt. Ltd., Mumbai; K. R. Kirtikar in Indian Medicinal Plants (1975) Vol. 2, p. 1225, published by Bishen Singh Mahendrapal Singh, Dehradun; P. K. Warrier in Indian Medicinal Plants- A compendium of 500 species (1994-1996) Vol. 2, p. 184, published by orient Longman, Chennai, and The Wealth of India (1950-1980) Vol. 3, p. 349, published by Council of Scientific and Industrial Research for the various medicinal properties of *Coriandrum sativum*.

Reference may be made to P. K. Warrier in Indian Medicinal Plants- A compendium of 500 species (1994-1996) Vol. 2, p. 277, published by orient Longman for the various medicinal properties of *Cyclea peltata*.

References may be made to K. M. Nadkarni in Indian Materia Medica (1976) Vol. 1, p. 537, published by Popular Prakashan Pvt. Ltd., Mumbai; K. R. Kirtikar in Indian Medicinal Plants (1975) Vol. 2, p. 1217, published by Bishen Singh Mahendrapal Singh, Dehradun; P. K. Warrier in Indian Medicinal Plants- A compendium of 500 species (1994-1996) Vol. 3, p. 13, published by orient Longman, Chennai; Y. K. Sarin in Illustrated lanual of herbal drugs used in Ayurveda (1996), p. 332, and The Ayurvedic Pharmacopoeia of India, p. 50, published by Ministry of Health and Family Welfare, India for the various medicinal properties of *Ferula asafoetida*.

The composition of the present invention should not be treated as an obvious one as none of the citations are able to provide all the advantages of the present invention.

OBJECTS OF THE INVENTION

The main object of the present invention is to provide a synergistic herbal composition for the treatment of gastric ulcer Yet another object of the present invention is to provide a process for the preparation of the composition.

Still another object of the present invention is to provide a method for the treatment of gastric ulcer using the composition.

SUMMARY OF THE INVENTION

The present invention provides a synergistic herbal composition for the treatment of gastric ulcer. Also, the present invention provides a process for the preparation of the composition. The present invention further provides a method for the treatment of gastric ulcer using said composition.

DETAILED DESCRIPTION OF THE PRESENT INVENTION

In accordance with the first embodiment of the present invention, there is provided a synergistic herbal composition for the treatment of gastric ulcer, said composition essentially comprising of powdered plant parts of *Asparagus racemosus, Glycyrrhiza glabra, Sesamum indicum, Musa sapientum* and *Trachyspermum roxburghianum* and optionally, powdered plant parts of *Cyclea peltata, Embelia ribes, Coriandrum sativum, Ferula asafoetida, Aloe barbadensis* and *Evolvulus alsinoides* along with one or more pharmaceutically acceptable additives/carriers.

In an embodiment of the present invention, the composition comprises powdered plant parts of *Asparagus racemosus, Glycyrrhiza glabra, Sesamum indicum, Musa sapientum* and *Trachyspermum roxburghianum* in equal proportions, optionally along with one or more pharmaceutically acceptable additives/carriers. This composition is hereafter referred to as HF3.

In another embodiment of the present invention, the composition comprises powdered plant parts of *Asparagus racemosus, Glycyrrhiza glabra, Sesamum indicum, Musa sapientum, Trachyspermum roxburghianum, Evolvulus alsinoides* and *Ferula asafoetida* in equal proportions, optionally along with one or more pharmaceutically acceptable additives/carriers. This composition is hereafter referred to as HF4.

In yet another embodiment of the present invention, the composition comprises powdered plant parts of *Asparagus racemosus, Glycyrrhiza glabra, Sesamum indicum, Musa sapientum, Trachyspermum roxburghianum, Evolvulus alsinoides, Ferula asafoetida, Coriandrum sativum, Cyclea peltata* and *Aloe barbadensis* in equal proportions, optionally along with one or more pharmaceutically acceptable additives/carriers. This composition is hereafter referred. to as HF5.

In still another embodiment of the present invention, the composition comprises 5-13 wt. % of powdered plant parts of *Asparagus racemosus*, 5-12 wt. % of powdered plant parts of *Glycyrrhiza glabra*, 8-14 wt. % of powdered plant parts of *Sesamum indicum*, 7-14 wt. % of powdered plant parts of *Musa sapientum*, 4-12 wt. % of powdered plant parts of *Trachyspermum roxburghianum*, 6-12 wt. % of powdered plant parts of *Aloe barbadensis*, 5-12 wt. % of powdered plant parts of *Evolvulus alsinoides*, 6-13 wt. % of powdered plant parts of *Cyclea peltala*, 9-14 wt. % of powdered plant parts of *Embelia ribes*, 7-14 wt. % of powdered plant parts of *Coriandrum sativum* and 8-13 wt. % of plant parts of *Ferula asafoetida*, optionally along with one or more pharmaceutically acceptable additives/carriers. This composition is hereafter referred to as HF2.

In one more embodiment of the present invention, the plant part of *Trachyspermum roxburghianum, Embelia ribes* and *Coriandrum sativum* is fruit.

In one another embodiment of the present invention, the plant part of *Cyclea peltata* and *Glycyrrhiza glabra* is root.

In a further embodiment of the present invention, the plant part of *Aloe barbadensis* is elio. In a furthermore embodiment of the present invention, the plant part of *Asparagus racemosus* is tuber.

In an embodiment of the present invention, the plant part of *Sesamum indicum* is seed. In another embodiment of the present invention, the plant part of *Musa sapientum* is unripe fruit.

In yet another embodiment of the present invention, the plant part of *Ferula asafoetida* is resin.

In accordance with the another embodiment of the present invention, there is provided a synergistic herbal composition for the treatment of gastric ulcer, said composition comprising equal proportions of 10 powdered plant parts selected from the group comprising of powdered plant parts of *Asparagus racemosus, Glycyrrhiza glabra, Sesamum indicum, Musa sapientum, Trachyspermum roxburghianum, Cyclea peltata, Embelia ribes, Coriandrum sativum, Ferula asafoetida, Aloe barbadensis* and *Evolvulus alsinoides*, optionally along with one or more pharmaceutically acceptable additives/carriers.

In an embodiment of the present invention, said composition comprises equal proportions of powdered plant parts of *Asparagus racemosus, Glycyrrhiza glabra, Sesamum indicum, Musa sapientum, Trachyspermum roxburghianum, Cyclea peltata, Embelia ribes, Coriandrum sativum, Ferula asafoetida* and *Aloe barbadensis*, optionally along with one or more pharmaceutically acceptable additives/carriers.

In another embodiment of the present invention, said composition comprises equal proportions of powdered plant parts of *Asparagus racemosus, Glycyrrhiza glabra, Sesamum indicum, Musa sapientum, Trachyspermum roxburghianum, Cyclea peltata, Embelia ribes, Coriandrum sativum, Ferula asafoetida* and *Evolvulus alsinoides*, optionally along with one or more pharmaceutically acceptable additives/carriers.

In yet another embodiment of the present invention, said composition comprises equal proportions of powdered plant parts of *Asparagus racemosus, Glycyrrhiza glabra, Sesamum indicum, Musa sapientum, Trachyspermum roxburghianum, Cyclea peltata, Embelia ribes, Coriandrum sativum, Aloe barbadensis* and *Evolvulus alsinoides*, optionally along with one or more pharmaceutically acceptable additives/carriers.

In still another embodiment of the present invention, said composition comprises equal proportions of powdered plant parts of *Asparagus racemosus, Glycyrrhiza glabra, Sesamum indicum, Musa sapientum, Trachyspermum roxburghianum, Cyclea peltata, Embelia ribes, Ferula asafoetida, Aloe bar-

*badensis* and *Evolvulus alsinoides*, optionally along with one or more pharmaceutically acceptable additives/carriers.

In one more embodiment of the present invention, said composition comprises equal proportions of powdered plant parts of *Asparagus racemosus, Glycyrrhiza glabra, Sesamum indicum, Musa sapientum, Trachyspermum roxburghianum, Cyclea peltata, Coriandrum sativum, Ferula asafoetida, Aloe barbadensis* and *Evolvulus alsinoides*, optionally along with one or more pharmaceutically acceptable additives/carriers.

In one another embodiment of the present invention, said composition comprises equal proportions of powdered plant parts of *Asparagus racemosus, Glycyrrhiza glabra, Sesamum indicum, Musa sapientum, Trachyspermum roxburghianum, Embelia ribes, Coriandrum sativum, Ferula asafoetida, Aloe barbadensis* and *Evolvulus alsinoides*, optionally along with one or more pharmaceutically acceptable additives/carriers.

In a further embodiment of the present invention, said composition comprises equal proportions of powdered plant parts of *Asparagus racemosus, Glycyrrhiza glabra, Sesamum indicum, Musa sapientum, Cyclea peltata, Embelia ribes, Coriandrum sativum, Ferula asafoetida, Aloe barbadensis* and *Evolvulus alsinoides*, optionally along with one or more pharmaceutically acceptable additives/carriers.

In a further more embodiment of the present invention, said composition comprises equal proportions of powdered plant parts of *Asparagus racemosus, Glycyrrhiza glabra, Sesamum indicum, Trachyspermum roxburghianum, Cyclea peltata, Embelia ribes, Coriandrum sativum, Ferula asafoetida, Aloe barbadensis* and *Evolvulus alsinoides*, optionally along with one or more pharmaceutically acceptable additives/carriers.

In an embodiment of the present invention, said composition comprises equal proportions of powdered plant parts of *Asparagus racemosus, Glycyrrhiza glabra, Musa sapientum, Trachyspermum roxburghianum, Cyclea peltata, Embelia ribes, Coriandrum sativum, Ferula asafoetida, Aloe barbadensis* and *Evolvulus alsinoides*, optionally along with one or more pharmaceutically acceptable additives/carriers.

In another embodiment of the present invention, said composition comprises equal proportions of powdered plant parts of *Asparagus racemosus, Sesamum indicum, Musa sapientum, Trachyspermum roxburghianum, Cyclea peltata, Embelia ribes, Coriandrum sativum, Ferula asafoetida, Aloe barbadensis* and *Evolvulus alsinoides*, optionally along with one or more pharmaceutically acceptable additives/carriers.

In yet another embodiment of the present invention, said composition comprises equal proportions of powdered plant parts of *Glycyrrhiza glabra, Sesamum indicum, Musa sapientum, Trachyspermum roxburghianum, Cyclea peltata, Embelia ribes, Coriandrum sativum, Ferula asafoetida, Aloe barbadensis* and *Evolvulus alsinoides*, optionally along with one or more pharmaceutically acceptable additives/carriers.

In accordance with the second embodiment of the present invention, there is provided a process for the preparation of the synergistic herbal composition for the treatment of gastric ulcer, said process comprising the steps of powdering plant parts essentially selected from *Asparagus racemosus, Glycyrrhiza glabra, Sesamum indicum, Musa sapientum* and *Trachyspermum roxburghianum* and optionally, selected from *Cyclea peltata, Embelia ribes, Coriandrum sativum Ferula asafoetida, Aloe barbadensis* and *Evolvulus alsinoides*, mixing the aforesaid powdered plant parts to obtain a mixture and optionally adding one or more pharmaceutically acceptable additives/carriers to the above mixture.

In an embodiment of the present invention, said process comprises the steps of powdering plant parts of *Asparagus racemosus, Glycyrrhiza glabra, Sesamum indicum, Musa sapientum* and *Trachyspermum roxburghianum*, mixing the aforesaid plant parts in equal proportions to obtain a mixture and optionally adding one or more pharmaceutically acceptable additives/carriers to the above mixture.

In another embodiment of the present invention, said process comprises the steps of powdering plant parts of *Asparagus racemosus, Glycyrrhiza glabra, Sesamum indicum, Musa sapientum, Trachyspermum roxburghianum, Evolvulus alsinoides* and *Ferula asafoetida*, mixing the aforesaid plant parts in equal proportions to obtain a mixture and optionally adding one or more pharmaceutically acceptable additives/carriers to the above mixture.

In yet another embodiment of the present invention, said process comprises steps of powdering plant parts of *Asparagus racemosus, Glycyrrhiza glabra, Sesamum indicum, Musa sapientum, Trachyspermum roxburghianum, Evolvulus alsinoides, Ferula asafoetida, Coriandrum sativum, Cyclea peltata* and *Aloe barbadensis*, mixing the aforesaid plant parts in equal proportions to obtain a mixture and optionally adding one or more pharmaceutically acceptable additives/carriers to the above mixture.

In still another embodiment of the present invention, said process comprises the steps of powdering and mixing 5-13 wt. % of plant parts of *Asparagus racemosus*, 5-12 wt. % of plant parts of *Glycyrrhiza glabra*, 8-14 wt. % of plant parts of *Sesamum indicum*, 7-14 wt. % of plant parts of *Musa sapientum*, 4-12 wt. % of plant parts of *Trachyspermum roxburghianum*, 6-12 wt. % of plant parts of *Aloe barbadensis*, 5-12 wt. % of plant parts of *Evolvulus alsinoides*, 6-13 wt. % of plant parts of *Cyclea peltata* 9-14 wt. % of plant parts of *Embelia ribes*, 7-14 wt. % of plant parts of *Coriandrum sativum* and 8-13 wt. % of plant parts of *Ferula asafoetida* to obtain a mixture and optionally adding one or more pharmaceutically acceptable additives/carriers to the above mixture.

In one more embodiment of the present invention, the plant part of *Trachyspermum roxburghianum, Embelia ribes* and *Coriandrum sativum* is fruit.

In one another embodiment of the present invention, the plant part of *Cyclea peltata* and *Glycyrrhiza glabra* is root.

In a further embodiment of the present invention, the plant part of *Aloe barbadensis* is elio. In a furthermore embodiment of the present invention, the plant part of *Asparagus racemosus* is tuber.

In an embodiment of the present invention, the plant part of *Sesamum indicum* is seed. In another embodiment of the present invention, the plant part of *Musa sapientum* is unripe fruit.

In yet another embodiment of the present invention, the plant part of *Ferula asafoetida* is resin.

In accordance with another object of the present invention, there is provided a method of treating gastric ulcer in a subject, said method comprising administering an effective amount of the synergistic herbal composition essentially comprising of powdered plant parts of *Asparagus racemosus, Glycyrrhiza glabra, Sesamum indicum, Musa sapientum* and *Trachyspermum roxburghianum* and optionally, powdered plant parts of *Cyclea peltata, Embelia ribes, Coriandrum sativum Ferula asafoetida, Aloe barbadensis* and *Evolvulus alsinoides* along with one or more pharmaceutically acceptable additives/carriers.

In an embodiment of the present invention, said method comprises administering an effective amount of the synergistic herbal composition comprising of powdered plant parts of *Asparagus racemosus, Glycyrrhiza glabra, Sesamum indicum, Musa sapientum* and *Trachyspermum roxburghianum* in equal proportions, optionally along with one or more pharmaceutically acceptable additives/carriers.

In another embodiment of the present invention, said method comprises administering an effective amount of the synergistic herbal composition comprising of powdered plant parts of *Asparagus racemosus, Glycyrrhiza glabra, Sesamum indicum, Musa sapientum, Trachyspermum roxburghianum, Evolvulus alsinoides* and *Ferula asafoetida* in equal proportions, optionally along with one or more pharmaceutically acceptable additives/carriers.

In yet another embodiment of the present invention, said method comprises administering an effective amount of the synergistic herbal composition comprising of powdered plant parts of *Asparagus racemosus, Glycyrrhiza glabra, Sesamum indicum, Musa sapientum, Trachyspermum roxburghianum, Evolvulus alsinoides, Ferula asafoetida, Coriandrum sativum, Cyclea peltata* and *Aloe barbadensis* in equal proportions, optionally along with one or more pharmaceutically acceptable additives/carriers.

In still another embodiment of the present invention, said method comprises administering an effective amount of the synergistic herbal composition comprising 5-13 wt. % of powdered plant parts of *Asparagus racemosus*, 5-12 wt. % of powdered plant parts of *Glycyrrhiza glabra*, 8-14 wt. % of powdered plant parts of *Sesamum indicum*, 7-14 wt. % of powdered plant parts of *Musa sapientum*, 4-12 wt. % of powdered plant parts of *Trachyspermum roxburghianum*, 6-12 wt. % of powdered plant parts of *Aloe barbadensis*, 5-12 wt. % of powdered plant parts of *Evolvulus alsinoides*, 6-13 wt. % of powdered plant parts of *Cyclea peltata* 9-14 wt. % of powdered plant parts of *Embelia ribes*, 7-14 wt. % of powdered plant parts of *Coriandrum sativum* and 8-13 wt. % of plant parts of *Ferula asafoetida* in equal proportions, optionally along with one or more pharmaceutically acceptable additives/carriers.

In one more embodiment of the present invention, the subject is a mammal including human.

In one another embodiment of the present invention, the effective dosage of the composition per day is in the range of 5 to 15 g.

In a further embodiment of the present invention, the composition can be in the form of tablets, capsules, syrup and any other conventional forms.

In a furthermore embodiment of the present invention, the composition is administered orally, intramuscularly, and by any other conventional methods.

In an embodiment of the present invention, the composition may be used for therapeutic as well as prophylactic treatment of gastric ulcer.

In another embodiment of the present invention, the subject may be administered a bolus dose or a multiple dose.

In yet another embodiment of the present invention, wherein the composition HF2 showed more than 62% protection against cold restraint ulcer model.

In still another embodiment of the present invention, wherein the composition HF2 showed more than 30 % protection against aspirin induced ulcer model.

In one more embodiment of the present invention, wherein the composition HF2 reduced the length of hemorrhagic bands to 22.67±4.69 (mm±SE) against alcohol induced gastric ulcer.

In one another embodiment of the present invention, wherein the composition HF2 has protection index greater than 80 against pyloric ligation induced ulcer.

BRIEF DESCRIPTION OF THE TABLES

In the tables accompanying the specification,

Table 1 represents the effect of the herbal composition HF2 prepared in accordance with one of the embodiments of the present invention and a standard drug "Omeprazole" against Cold Restraint (at 4° C. temp, for 2 hrs.) induced Ulcer (CRU).

Table 2 represents the effect of the herbal composition HF2 prepared in accordance with one of the embodiments of the present invention and the standard drug "Omeprazole" against aspirin induced gastric ulcer.

Table 3 represents the effect of the herbal composition HF2 prepared in accordance with one of the embodiments of the present invention and the standard drug "Omeprazole" against alcohol induced gastric ulcer in rats.

Table 4 represents the effect of the herbal composition HF2 prepared in accordance with one of the embodiments of the present invention and the standard drug "Omeprazole" against Histamine induced ulcer model.

Table 5 represents the effect of the herbal composition HF2 prepared in accordance with one of the embodiments of the present invention and a standard drug "Omeprazole" against Pyrolic ligation induced ulcer model.

Table 6 gives the composition of the Herbal composition HF2 prepared in accordance with one of the embodiments of the present invention.

Table 7 provides the antigastric ulcer activity of herbal compositions HF3, HF4 and HF5 prepared in accordance with the embodiments of the present invention against cold restrained ulcer model, pyloric ligation ulcer model and alcohol induced ulcer model.

Table 8 provides the results of the study conducted to evaluate the synergistic effect of the composition HF2.

Table 9 gives the composition of the Herbal compositions HF3, HF4 and HF5. The invention is further described with respect to the following experiments which are given by way of illustration and therefore should not be construed to limit the scope of the invention in any manner.

Experimental protocol:

Invivo experiments:

The Applicants have carried out several experiments under different induced ulcer conditions and the effect of the herbal composition were studied and are tabulated herebelow. The effect of the herbal composition has been compared with respect to a known anti-ulcer drug "Omeprazole".

EXPERIMENT 1: EFFECT ON COLD RESTRAINT ULCERS (CRU) MODEL

METHOD: Adult rats of either sex, weighing 150-175 Gms were fasted for 24 hours with free access to water. The test drugs were administered 45 minutes before immobilizing the animals. The rats were immobilized in the restraint cage at 4° C. in BOD incubator for 2 hrs and were sacrificed immediately after the restraint period. (According to the method of Senay and Levine 1967). The abdomen was cut opened; stomach was taken out and incised along the greater curvature to observe the gastric lesions with the help of Magnascope (5×magnification).

The following arbitrary scoring system was used to grade the severity and intensity of the lesions.

1. Shedding of epithelium=10
2. Petechial and frank hemorrhages=20
3. One or two ulcers=30
4. More than two ulcers=40
5. Perforated ulcers=50

The presence of any of these lesions was considered as a positive ulcerogenic response which has been shown as percentage of rats showing gastric lesions.

The severity of ulcers is expressed in terms of ulcer index, which is the mean score of gastric lesions of all the rats in a group which is defined as:

Ulcer Index (U.I.)=Us+Up×10$^{-1}$

Where Us=Mean severity of ulcer score and Up—Percentage of animals with Ulcer incidences The percentage protection is calculated as follows:
Percentage protection=(C-T/C)×100.
Wherein
C=Number of animals showing ulcer response in control group and
T=Number of animals showing ulcer response in test group.

The effect of the Herbal Composition of the present invention hereafter referred to as "HF2" against Cold Restraint Ulcer Model (CRU) is given in Table 1. The effect of the standard drug "Omeprazole" is also given in Table 1.

provides significantly better protection against cold restraint ulcer model as compared to Omeprazole.

EXPERIMENT 2: EFFECT ON ASPIRIN INDUCED GASTRIC ULCER MODEL

METHOD: Gastric ulceration was induced by aspirin according to the method of Djahanguiri (1969). Aspirin (150 mp/Kg.) was administered per orally as a suspension in gum-acacia and the animal was sacrificed 5 hr. after the aspirin treatment and the ulcer index with protection index were calculated. The results of the experiment is tabulated in Table 2.

TABLE 1

THE EFFECT OF THE HERBAL COMPOSITION "HF2" AND THE STANDARD DRUG "OMEPRAZOLE" AGAINST COLD RESTRAINT ULCER MODEL (CRU).

| Compounds and Doses | Ulcer severity (type of lesions) Scores (No. of rats showing lesions/No. of rats tested) | | | | | Mean severity of ulcer score | Percentage of ulcer incidence (No. of rats showing ulcer/total No. of rats used) | Ulcer index | Protection index |
|---|---|---|---|---|---|---|---|---|---|
| | 10 | 20 | 30 | 40 | 50 | | | | |
| Control CRU | — | 6/10 | 4/10 | — | — | 24 | 100 (10/10) | 12.4 | 00 |
| CRU + HF2 (50 mg/Kg, p..o.) | 2/10 | 2/10 | — | — | — | 06 | 40 (4/10) | 4.6 | 62.90 |
| CRU + Omeprazole (10 mg/Kg, p.o.) | 3/10 | 2/10 | — | — | — | 07 | 50 (5/10) | 5.7 | 54.03 |

INFERENCE: Omeprazole showed 54.03% protection where as the composition HF2 showed 62.90%, protection against gastric ulcer. Thus it is clear that the composition HF2

The effect of the herbal composition HF2 and the standard drug "Omeprazole" against aspirin induced gastric ulcer is given in Table 2.

TABLE 2

THE EFFECT OF THE HERBAL COMPOSITION "HF2" AND THE STANDARD DRUG "OMEPRAZOLE" AGAINST ASPIRIN INDUCED GASTRIC ULCER

| Compounds and Doses | Ulcer severity (type of lesions) Scores (No. of rats showing lesions/No. of rats tested) | | | | | Mean severity of ulcer score | Percentage of ulcer incidence (No. of rats showing ulcer/total No. of rats used) | Ulcer index | Protection index |
|---|---|---|---|---|---|---|---|---|---|
| | 10 | 20 | 30 | 40 | 50 | | | | |
| Control Aspirin (150 mg/KG, p.o.) | — | 2/6 | 4/6 | — | — | 26.6 | 100 (6/6) | 12.66 | 00 |
| Aspirin + HF 2 (100 mg/Kg, p.o.) | 2/6 | 2/6 | — | — | — | 10..0 | 66.7 (4/6) | 7.67 | 39.41 |
| Aspirin + Omeprazole (10 mg/Kg, p.o.) | 2/6 | 2/6 | — | — | — | 10.0 | 66.7 (4/6) | 7.67 | 39.41 |

INFERENCE: Both Omeprazole and the composition HF2 showed equal protection (39.41% protection) against aspirin induced ulcer model.

EXPERIMENT 3: EFFECT ON ALCOHOL INDUCED GASTRIC ULCERS IN RATS

METHOD: Adult rats of either sex were taken; weighing 150-175 grams were fasted for 24 hours with fire access to water. The test drugs were administered (p.o.) 45 minutes before alcohol administration. 1 ml of chilled absolute alcohol was amine (p.o.) to the rats (According to Wittetal)[3]. Immediately after 1 hour, the animals were anesthetized, abdomen was cut opened stomach was taken out and incised along the greater curvature to observe the gastric lesions. The ulcers are examined under the 5X magnification with the help of magnascope. Absolute ethanol lesions appears as blackish lesions grouped in patches of varying size, usually parallel to the major axis of the stomach. The lengths of the lesions are measured and summated to give a total lesion score, then calculated and expressed in percentage.

The effect of the herbal composition "HF2" and the standard drug "Omeprazole" against alcohol induced gastric ulcer in rats is given in Table 3.

TABLE 3

THE EFFECT OF THE HERBAL COMPOSITION "HF2" AND THE STANDARD DRUG "OMEPRAZOLE" AGAINST ALCOHOL INDUCED GASTRIC ULCER IN RATS

| Compound | Length of hemorrhagic bands (mm ± SE) |
|---|---|
| Ethanol control | 73.5 ± 1.5 |
| HF 2 (100 mg/kg, p.o.) + Ethanol | 22.67 ± 4.69 |
| Omeprazole (100 mg/kg, p.o.) + Ethanol | 56.0 ± 9.12 |

INFERENCE: The composition of the present invention showed significant protection against this model also. The protection provided by the composition of the present invention is better than Omeprazole.

EXPERIMENT 4: EFFECT ON HISTAMINE INDUCED ULCER MODEL

METHOD: Animals were fasted for 24 hours with access to water. The drug was given orally 1 hour prior to the histamine administration. Histamine was administered in a dose of 0.25 mg/Kg, i.m. at 30 minutes interval -for 7 times and it induced 100% duodenal ulceration in guinea pig (According to the method of Watt and Eagleton 1964)[4]. The animals were sacrificed after half an hour of last injection under ether anesthesia. The stomach along with duodenum was removed washed thoroughly and examined for the lesions and ulcer index with protection index was calculated. The results of the experiment are tabulated in Table 4. The effect of the herbal composition "HF2" and the standard drug "Omeprazole" against Histamine induced ulcer model is given in Table 4.

TABLE 4

THE EFFECT OF THE HERBAL COMPOSITION "HF2" AND THE STANDARD DRUG "OMEPRAZOLE" AGAINST HISTAMINE INDUCED ULCER MODEL

| Groups and doses of compounds | Ulcer severity (type of lesions) Scores (No. Guinea pig showing lesions/No. of Guinea pig tested) | | | | | Mean severity of ulcer score | Percentage of ulcer incidence (No. of animals showing ulcer/ total No. of animals used) | Ulcer index | % Protection | Volume of gastric fluid (mL) |
|---|---|---|---|---|---|---|---|---|---|---|
| | 10 | 20 | 30 | 40 | 50 | | | | | |
| Ulcer Control Histamine (0.25 mg/Kg, i.m.) × 7 | — | — | 1/3 | 2/3 | — | 36.6 | 100 (3/3) | 13.66 | 00 | 4.33 ± 1.01 |
| Histamine + HF2 (50 mg/Kg, p.o.) | — | — | 1/3 | — | — | 10.0 | 33.3 (1/3) | 4.33 | 68.3 | 1.60 ± 0.7 |
| Histamine + Omeprazole (10 mg/kg, p.o.) | — | 1/3 | — | — | — | 6.66 | 33.3 (1/3) | 3.99 | 70.79 | 1.0 ± 0.2 |

INFERENCE: In this model, Omeprazole showed 70.79% protection whereas the composition HF2 showed 68.3% protection. In comparison, the composition HF2 provides more or less equal protection.

EXPERIMENTS 5: EFFECT ON PYLORIC LIGATION INDUCED ULCER MODEL

METHOD: Animals were fasted for 24 hours in the raised mesh bottom cages to prevent coprophagia and were allowed free access to water. The control group of rats was feed with the vehicle and the experimental groups with their respective drugs 45 minutes prior to the ligation. The animal was anesthetized, abdomen was cut opened under xiphoid process, and the pyloric portion of the stomach was slightly liked and ligated avoiding any damage to the adjacent blood vessels (According to the method of Shay et al. 1945). The animals were stitched and kept for 4 hours with free access to water. After 4 hours the animals were sacrificed under ether anesthesia and the stomach was dissected out incised along the greater curvature. The stomach was washed thoroughly and the ulcer index was scored as per in other ulcer models. The results of the experiment are tabulated in Table 5.

The effect of the herbal composition "HF2" and the standard drug "Omeprazole" against Pyloric ligation induced ulcer model is given in Table 5.

TABLE 5

EFFECT OF OMEPRAZOLE AND THE HERBAL COMPOSITION HF2 AGAINST PYLORIC LIGATION INDUCED ULCER

| Groups | Ulcer Index | Protection Index |
|---|---|---|
| Ligation Control | 16.6 | 0.0 |
| Ligation + HF2 | 1.65 | 84.08 |

TABLE 5-continued

EFFECT OF OMEPRAZOLE AND THE HERBAL COMPOSITION
HF2 AGAINST PYLORIC LIGATION INDUCED ULCER

| Groups | Ulcer Index | Protection Index |
|---|---|---|
| Ligation + Omeprazofe (10 mg/Kg, p.o.) | 6.6 | 51.44 |

INFERENCE: The composition of the present invention showed better protection than Omeprazole in the pyloric ligation induced ulcer model.

EXPERIMENT 6: EFFECT OF THE PRESENT COMPOSITION ON ACETYLCHOLINE AND HISTAMINE INDUCED CONTRACTION OF GUINEA-PIG ILEUM

METHOD: A piece of 2-3 cm of the terminal ileum of a freshly killed Guinea pig was ended in an organ bath containing Tyrode solution at 34° C. and bubbled with fresh air. Contraction was induced by submaximal contraction of acetylcholine chloride (1 [ig/mL) and Histamine (1 ng/mL) and it was recorded on a kymograph (According to the method of Patnaik 1992). The composition HF2 (up to 250 ng/mL) did not exert any significant influence on isolated tissue preparation for anticholinergic (acetylcholine-induced contraction of Guinea-pig ileum) and Fk-anti-histaminic (Histamine induced contraction of Guinea-pig ileum) activity.

EXPERIMENT 7: HERBS AND PREPARATION OF THE COMPOSITION

For the purpose of conducting animal experiment all the herbs are washed dried and pulverised. All the herbs are taken in the proportion as shown in Table 6. The whole mixture is blended well and used for administering.

The components and their proportions of the standard herbal composition according to one embodiment of the present invention are listed in Table 6. The part of the herb which is used is also mentioned. The placebo preparation is designed to taste, smell and look like an Ayurvedic herbal composition.

TABLE 6

THE COMPOSITION OF THE HERBAL COMPOSITION HF2

| S. No. | Name of the plant and its part used | Percentage |
|---|---|---|
| 1. | *Aloe barbadensis* (elio) | 6-12% |
| 2. | *Asperagus racemosus* (Tubers) | 5-13% |
| 3. | *Glycyrrhiza glabra* (roots) | 5-12% |
| 4. | *Seaamum indicum* (seeds) | 8-14% |
| 5. | *Evolvulus aisinodes* (whole plant) | 5-12% |
| 6. | *Musa sapientum* (unripe fruit) | 7-14% |
| 7. | *Trachyaparmum roxburghicinum* (fruits) | 4-12% |
| 8. | *Embelia ribes* (fruits) | 9-14% |
| 9. | *Coriandrum sativum* (fruits) | 7-14% |
| 10. | *Cyclea peltate* (root) | 6-13% |
| 11. | *Ferula asafoetida* (resin) | 8-13% |

TABLE 7

ANTIGASTRIC ULCER ACTIVITY OF THE HERBAL
COMPOSITIONS HF3, HF4 AND HF5

| Formulation | Cold restrained ulcer model | Pyloric ligation model | Alcohol induced ulcer model |
|---|---|---|---|
| HF3 | 66.69 | 41.75 | 86.54 |
| HF4 | 45.86 | 17.0 | 79.42 |
| HF5 | 45.86 | 62.75 | 85.75 |

In order to conduct a study on the synergistic effect, the herbal composition HF2 was taken and each component was removed and the effect of the resultant composition against cold restrained gastric ulcer model was studied. The results of the experiment thus conducted is tabulated in Table 8. It was concluded from the above experiments that the batch prepared by the removal of Emblica ribes has shown very good protection.

TABLE 8

RESULTS OF THE SYNERGISTIC EFFECT STUDY

| S. No. | Details of Batch | Ulcer Index |
|---|---|---|
| 1 | HF2 without *Aloe barbadensis* | 26.6 |
| 2 | HF2 without *Asperagus racemosus* | 11.6 |
| 3 | HF2 without *Glycyrrhiza glabra* | 15.0 |
| 4 | HF2 without *Seamum indicum* | 20.0 |
| 5 | HF2 without *Evolvulus alisinoides* | 13.3 |
| 6 | HF2 without *Trachyspermum roxhurghianum* | 20.0 |
| 7 | HF2 without *Embelica ribes* | 8.3 |
| 8 | HF2 without *Coriandrum sativum* | 10.0 |
| 9 | HF2 without *Cyclea peltata* | 11.66 |
| 10 | HF2 without *Ferula asafetida* | 13.0 |
| 11 | HF2 without *Musa sapientum* | 20.0 |

TABLE 9

COMPOSITION OF THE HERBAL COMPOSITIONS HF3,
HF4 AND HF5

| HF3 | HF4 | HF5 |
|---|---|---|
| 1. *Asperagus racemosus* | 1. *Asperagus racemosus* | 1. *Asperagus racemosus* |
| 2. *Glycyrrhiza glabra* | 2. *Glycyrrhiza glabra* | 2. *Glycyrrhiza glabra* |
| 3. *Seaamum indicum* | 3. *Seaamum indicum* | 3. *Seaamum indicum* |
| 4. *Musa sapientum* and | 4. *Musa sapientum* | 4. *Musa sapientum* |
| 5. *Trachyaparmum roxburghicinum* All in equal proportions | 5. *Trachyaparmum roxburghicinum* | 5. *Trachyaparmum roxburghicinum* |
| | 6. *Evolvulus aisinodes* and | 6. *Evolvulus alsinodes* |
| | 7. *Ferula asafoetida* All in equal proportions | 7. *Ferula asafoetida* |
| | | 8. *Coriandrum sativum* |
| | | 9. *Cyclea peltate* and |
| | | 10. *Aloe barbadensis* All in equal proportions |

The invention claimed is:

1. A herbal composition for the treatment of gastric ulcer, said composition comprising a powdered plant part of a plant selected from the group consisting of *Aparagus racemousus, Glycrrhiza glabra, Sesamum indicum, Musa sapientum, Trachyspermum roxburghianum, Cyclea peltata, Embelia ribes, Coriandrum sativum, Aloe barbadensis* and *Evolvulus alsinoides,* a resin from *Ferula asafoetida* and one or more pharmaceutically acceptable additives or carriers, wherein said composition comprises each of *Asparagus racemosus, Glycyrrhiza glabra, Sesamum indicum, Musa sapientum* and

*Trachyspermum roxburghianum* in about equal proportions by weight and such about equal proportion has a value greater than zero.

2. The composition as claimed in claim 1, wherein the composition comprises a powdered plant part of each of *Asparagus racemosus, Glycyrrhiza glabra, Sesamum indicum, Musa sapientum* and *Trachyspermum roxburghianum* in equal proportions by weight, and one or more pharmaceutically acceptable additives or carriers.

3. The composition as claimed in claim 1, wherein the composition comprises a powdered plant part of each of *Asparagus racemosus, Glycyrrhiza glabra, Sesamum indicum, Musa sapientum, Trachyspermum roxburghianum, Evolvulus alsinoides, Ferula asafoetida, Coriandrum sativum, Cyclea peltata* and *Aloe barbadensis* in equal proportions by weight, and one or more pharmaceutically acceptable additives or carriers.

4. The composition as claimed in claim 1, wherein the plant part of each of *Embelia ribes* and *Coriandrum sativum* is a fruit.

5. The composition as claimed in claim 1, wherein the plant part of *Cyclea peltata* and *Glycyrrhiza glabra* is a root.

6. The composition as claimed in claim 1, wherein the plant part of *Asparagus racemosus* is a tuber.

7. The composition as claimed in claim 1, wherein the plant part of *Sesamum indicum* is a seed.

8. The composition as claimed in claim 1, wherein the plant part of *Musa sapientum* is an unripe fruit.

* * * * *